US012569648B2

(12) United States Patent
Kisa

(10) Patent No.: US 12,569,648 B2
(45) Date of Patent: Mar. 10, 2026

(54) CATHETER AND METHOD FOR MANUFACTURING CATHETER

(71) Applicant: KANEKA CORPORATION, Osaka (JP)

(72) Inventor: Toshiya Kisa, Okaya (JP)

(73) Assignee: KANEKA CORPORATION, Osaka (JP)

( * ) Notice: Subject to any disclaimer, the term of this patent is extended or adjusted under 35 U.S.C. 154(b) by 953 days.

(21) Appl. No.: 17/716,076

(22) Filed: Apr. 8, 2022

(65) Prior Publication Data

US 2022/0226610 A1     Jul. 21, 2022

Related U.S. Application Data

(63) Continuation of application No. PCT/JP2020/034106, filed on Sep. 9, 2020.

(30) Foreign Application Priority Data

Oct. 9, 2019     (JP) ................................. 2019-185879

(51) Int. Cl.
  *A61M 25/01*       (2006.01)
  *A61M 25/00*       (2006.01)
       (Continued)
(52) U.S. Cl.
  CPC .... *A61M 25/0133* (2013.01); *A61M 25/0015* (2013.01); *A61M 25/01* (2013.01);
       (Continued)
(58) Field of Classification Search
  CPC .......... A61M 25/0133; A61M 25/0015; A61M 25/01; A61M 2025/0175; A61N 1/3621; A61N 1/365
  See application file for complete search history.

(56) References Cited

U.S. PATENT DOCUMENTS 5,871,444 A * 2/1999 Ouchi .................... A61B 5/287
                                                        600/374

FOREIGN PATENT DOCUMENTS

JP          9-253063  A     9/1997
JP       2012-176163  A     9/2012

OTHER PUBLICATIONS

International Search Report, issued in PCT/JP2020/034106, dated Nov. 17, 2020.

(Continued)

*Primary Examiner* — Linda C Dvorak
*Assistant Examiner* — Abigail Bock
(74) *Attorney, Agent, or Firm* — Birch, Stewart, Kolasch & Birch, LLP

(57)          ABSTRACT

This catheter has: a shaft (10) has a first side hole (31) and a second side hole (32) in a wall (12); an insertion member (20) disposed in the lumen (11) of the shaft (10); a first electrode (41) provided on outer side of the first side hole (31); and a first wire (51) that is electrically connected to the first electrode (41) through the first side hole (31) and extents in the lumen (11) of the shaft (10) but outside the insertion member (20), wherein the first wire (51) has a first position (61) and a second position (62) inside the shaft (10), and the second position (62) of the first wire (51) is located at a position deviated from the first position (61) by 45 degrees or more in a circumferential direction of the insertion member (20).

22 Claims, 8 Drawing Sheets

(51) Int. Cl.
    *A61N 1/362*       (2006.01)
    *A61N 1/365*       (2006.01)

(52) U.S. Cl.
    CPC ........... *A61N 1/3621* (2013.01); *A61N 1/365*
           (2013.01); *A61M 2025/0175* (2013.01)

(56)             References Cited

OTHER PUBLICATIONS

Written Opinion of the International Searching Authority, issued in
PCT/JP2020/034106, dated Nov. 17, 2020.

\* cited by examiner

[Fig. 1]
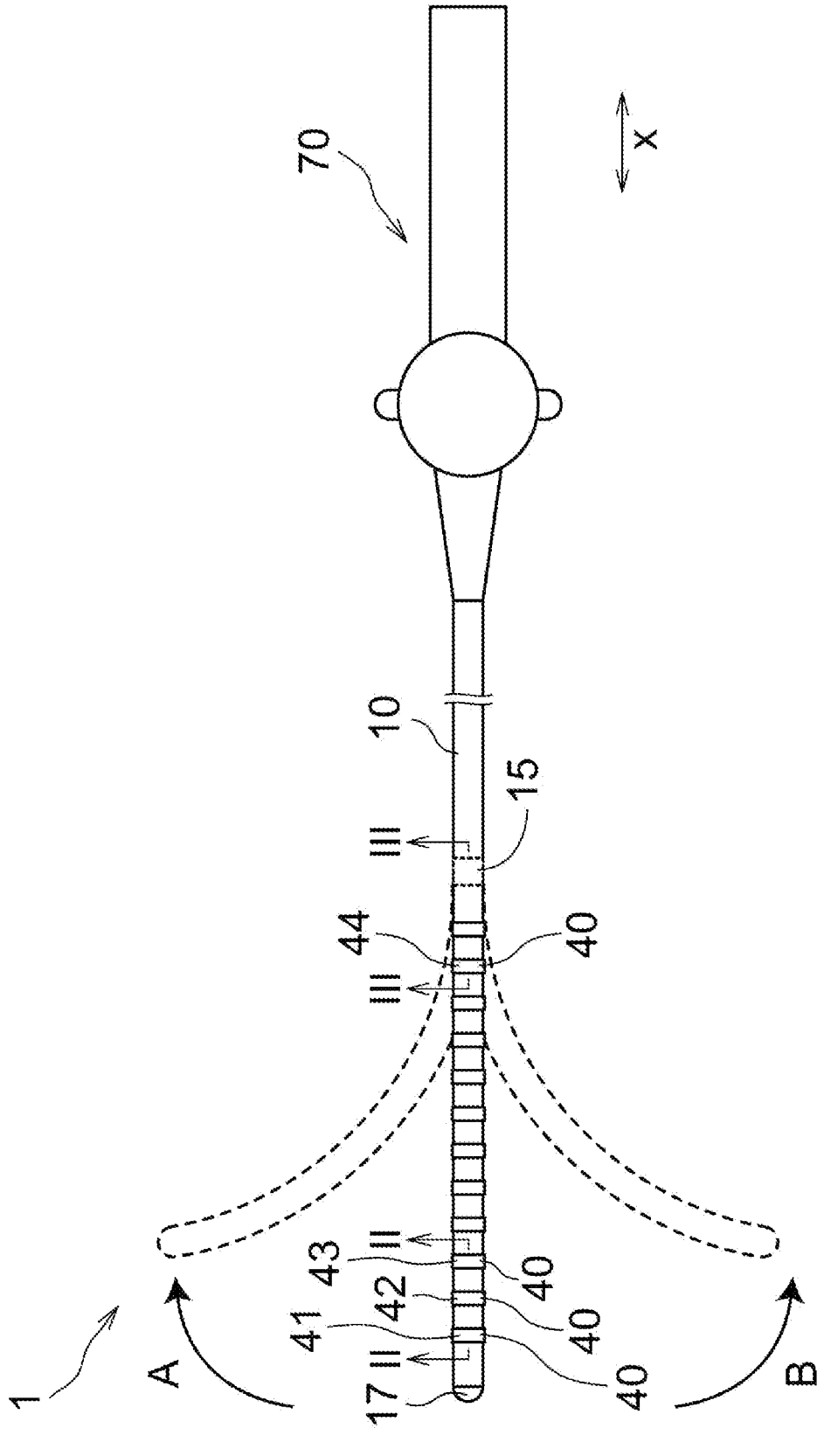

[Fig. 2]
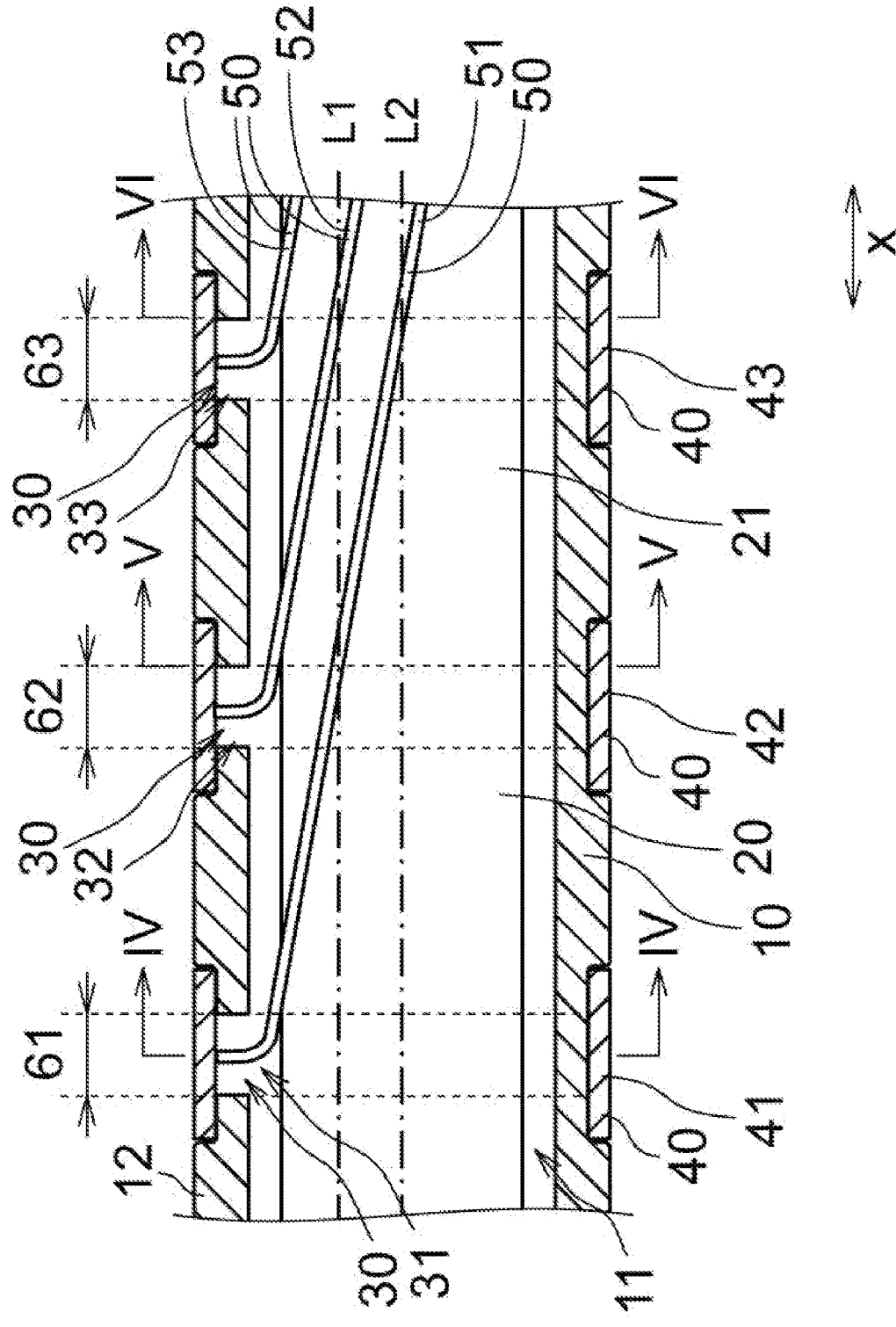

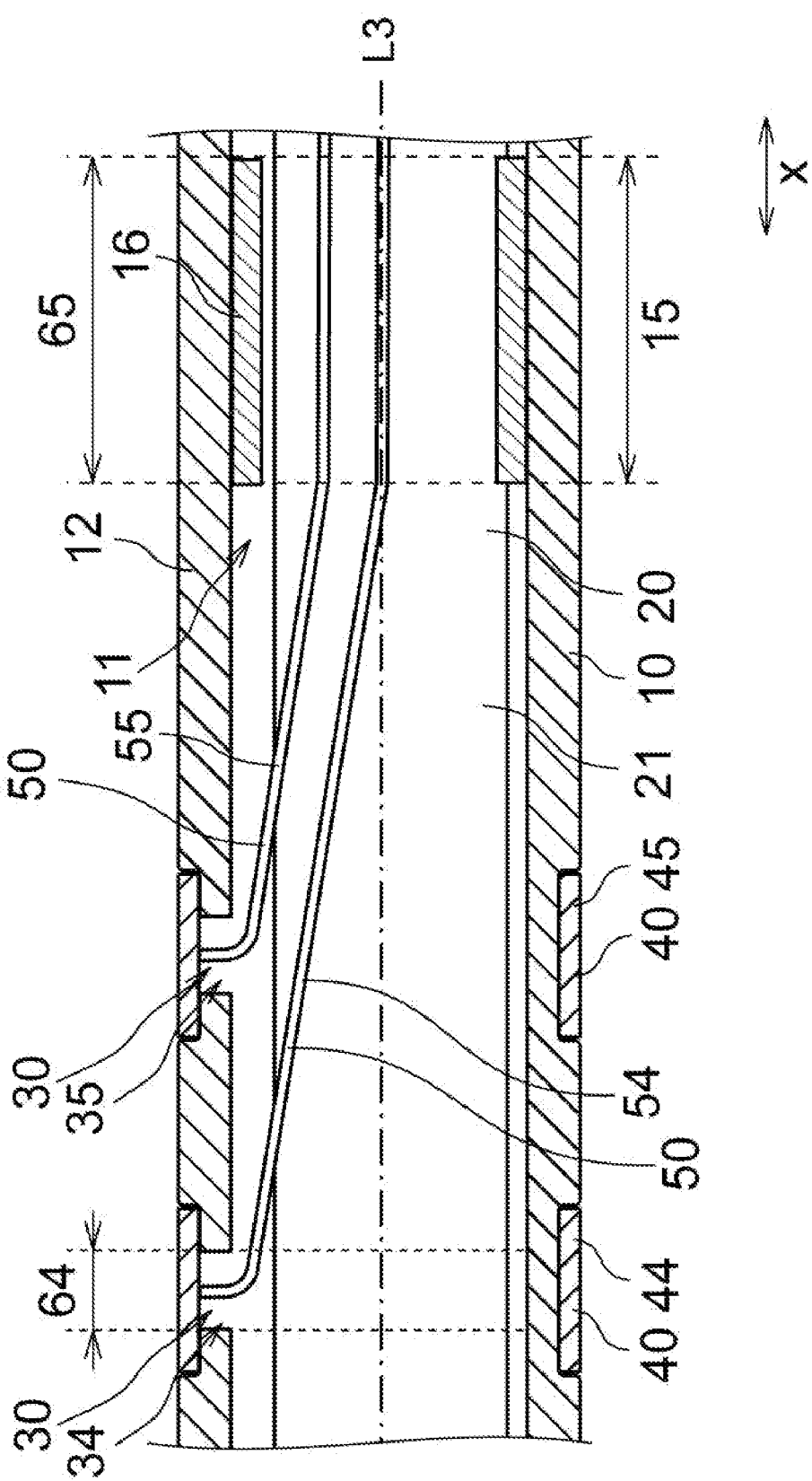
[Fig. 3]

[Fig. 4]
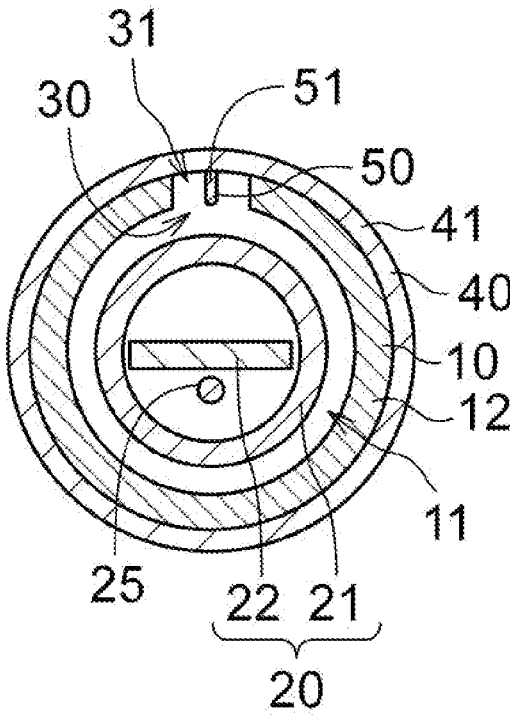
[Fig. 5]
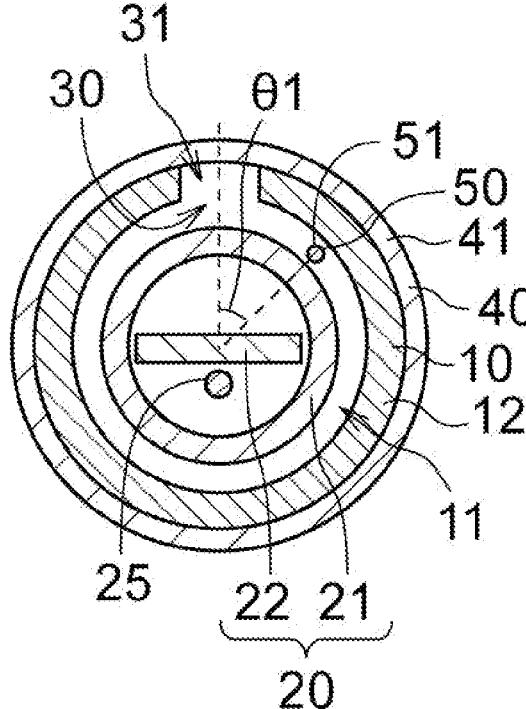

[Fig. 6]
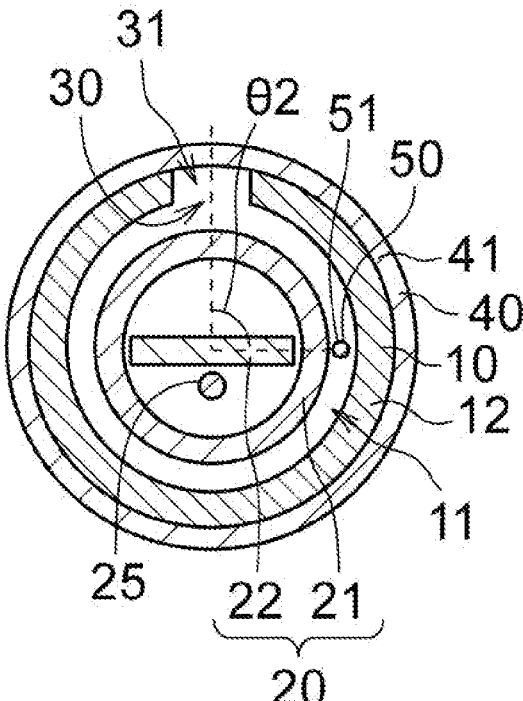
[Fig. 7]
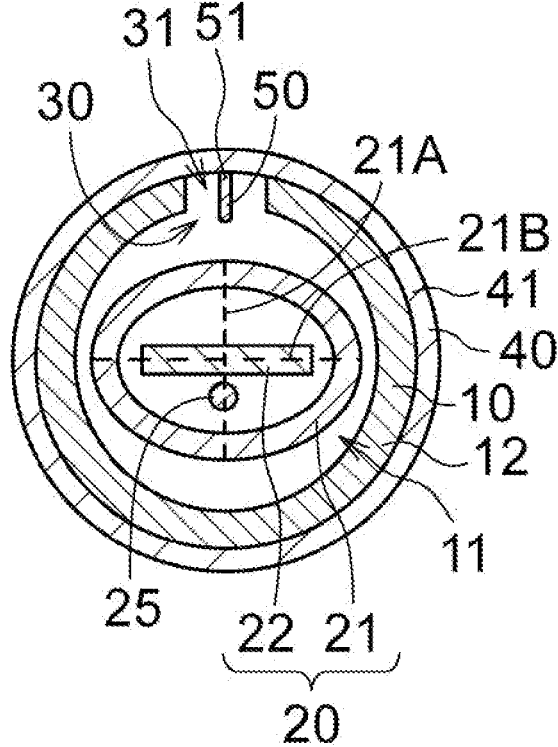

[Fig. 8]
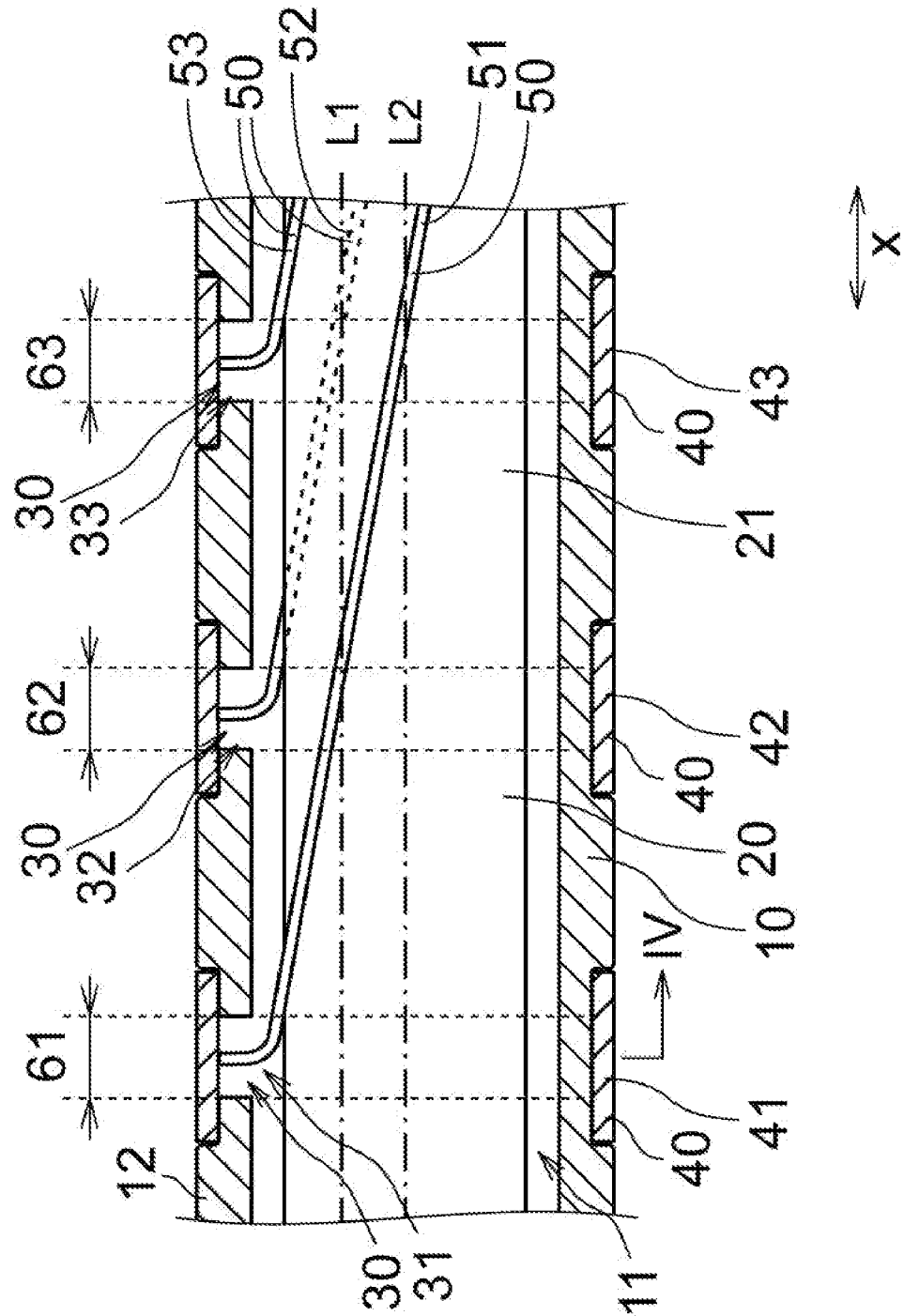

[Fig. 9]
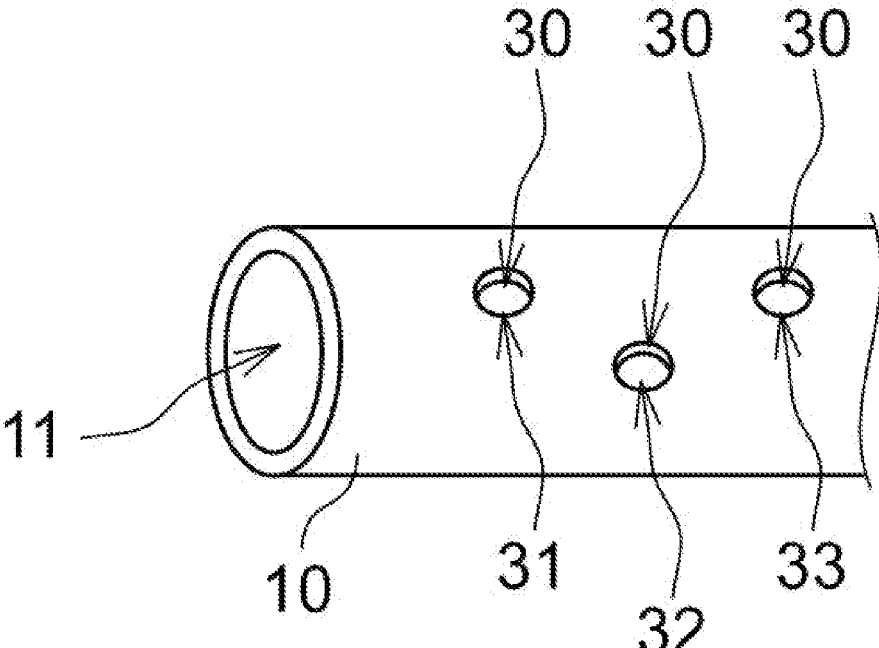
[Fig. 10]

[Fig. 11]
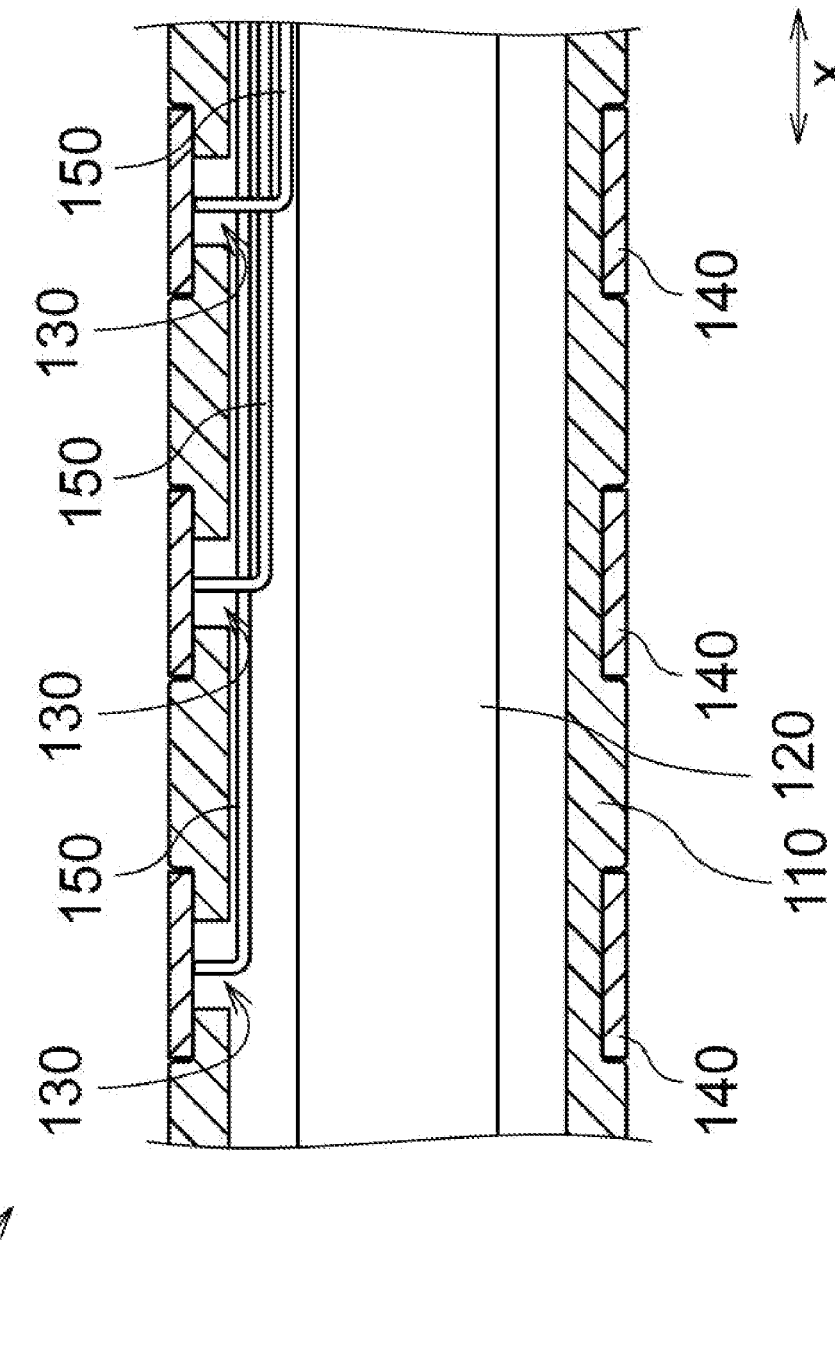

CATHETER AND METHOD FOR MANUFACTURING CATHETER

CROSS-REFERENCE TO RELATED APPLICATIONS

This application is a Continuation of PCT International Application No. PCT/JP2020/034106, filed on Sep. 9, 2020, which claims priority under 35 U.S.C. § 119(a) to Patent Application No. 2019-185879, filed in Japan on Oct. 9, 2019, all of which are hereby expressly incorporated by reference into the present application.

TECHNICAL FIELD

The present invention relates to an electrode catheter used to measure a potential of a body organ, mainly a heart and cauterize a body tissue, and a method for manufacturing the electrode catheter.

BACKGROUND ART

An electrode catheter, which is a catheter including an electrode on a shaft, is used as a medical instrument that mainly measures a potential of a heart to diagnose arrhythmia or cauterizes a body tissue by flowing a high-frequency current to treat arrhythmia. In the electrode catheter, a plurality of the electrodes are disposed on the outer side of the shaft having a lumen. A wire electrically connected to an inner surface of the electrode extends through the lumen of the shaft to an electrocardiograph. A connector is used to connect the wire and the electrocardiograph. Thus, it is possible to accurately grasp a state of a myocardium that causes arrhythmia by measuring an electrocardiogram in the vicinity of the electrode portion, for example, by inserting the electrode catheter into a heart of a patient and connecting the connector to the electrocardiograph. For example, Patent Document 1 discloses that an orientation of a distal end of an electrode catheter inserted into a heart can be changed.

RELATED ART DOCUMENTS

Patent Documents

Patent Document 1: JP-A-2012-176163

SUMMARY OF THE INVENTION

Technical Problem

As illustrated in FIG. 11, in a conventional catheter 101 as described above, a wire 150 connected to an electrode 140 is introduced into a shaft 110 through a side hole 130 provided in a wall of the shaft 110. In the shaft 110, the wire 150 is disposed to extend straight along a longitudinal axis direction x of the shaft 110. However, the wire 150 is made of metal and hardly stretches. Thus, when an attempt is made to curve a distal end portion of the catheter 101, the wire 150 props up, which may impair the flexibility of the distal end portion of the catheter 101. In particular, in a case where an insertion member 120 is provided in a lumen of the shaft 110 for the purpose of retaining a shape of a distal end portion of the shaft 110 during an operation or curving the distal end portion of the shaft 110 during the operation, the lumen of the shaft 110 is narrowed and the movement of the wire 150 is further restricted, so that the prop-up of the wire 150 easily occurs. Therefore, an object of the present invention is to provide a catheter capable of securing the flexibility of a distal end portion and a method for manufacturing the same.

Solutions to the Problems

A gist of one embodiment of a catheter of the present invention is to include: a shaft having a distal end and a proximal end in a longitudinal axis direction and a lumen extending in the longitudinal axis direction, the shaft having a wall having a first side hole and a second side hole provided adjacently in order from a distal side; an insertion member disposed in the lumen of the shaft; a first electrode provided on the outer side of the first side hole; and a first wire that is electrically connected to the first electrode and extends through the first side hole to the outer side of the insertion member in the lumen of the shaft, the first wire having a first position and a second position inside the shaft, the first position being located at the same position as the first side hole in the longitudinal axis direction of the shaft, the second position being located at the same position as the second side hole in the longitudinal axis direction of the shaft, and the second position of the first wire being located at a position deviated from the first position by 45 degrees or more in a circumferential direction of the insertion member. According to the catheter, since the first wire is disposed such that the second position is located at the position deviated from the first position by 45 degrees or more in the circumferential direction of the insertion member, it is possible to provide a margin for a length of the first wire in the lumen of the shaft. Thus, even if the first wire is dragged due to the curving of the shaft, such dragging can be absorbed by the extra length, so that the first wire can be prevented from propping up. Therefore, the flexibility of the distal end portion of the catheter can be secured.

A gist of another embodiment of a catheter of the present invention is to include: a shaft having a distal end and a proximal end in a longitudinal axis direction and a lumen extending in the longitudinal axis direction, the shaft having a wall having a first side hole, a second side hole, and a third side hole provided adjacently in order from a distal side; an insertion member disposed in the lumen of the shaft; a first electrode provided on the outer side of the first side hole; and a first wire that is electrically connected to the first electrode and extends through the first side hole to the outer side of the insertion member in the lumen of the shaft, the first wire having a first position, a second position, and a third position inside the shaft, the first position being located at the same position as the first side hole in the longitudinal axis direction of the shaft, the second position being located at the same position as the second side hole in the longitudinal axis direction of the shaft, the third position being located at the same position as the third side hole in the longitudinal axis direction of the shaft, and the third position of the first wire being located at a position deviated from the first position by 90 degrees or more in a circumferential direction of the insertion member. According to the catheter, since the first wire is disposed such that the third position is located at the position deviated from the first position by 90 degrees or more in the circumferential direction of the insertion member, it is possible to provide a margin for a length of the first wire in the lumen of the shaft. Thus, even if the first wire is dragged due to the curving of the shaft, such dragging can be absorbed by the extra length, so that the first wire can be prevented from propping up. Therefore, the flexibility of the distal end portion of the catheter can be secured.

The first wire is preferably wound around the outer side of the insertion member from the first position to the second position.

The catheter may further include a second electrode provided on an outer side of the second side hole; and a second wire that is electrically connected to the second electrode and extends through the second side hole to the outer side of the insertion member in the lumen of the shaft, wherein a third side hole is provided on the wall of the shaft on a proximal side of the second side hole, the second wire has a second position and a third position inside the shaft, the second position being located at a same position as the second side hole in the longitudinal axis direction, and the third position being located at a same position as the third side hole in the longitudinal axis direction, and the third position of the second wire is located at a position deviated from the second position by 45 degrees or more in the circumferential direction of the insertion member.

A direction in which the first wire is wound around the outer side of the insertion member from the first position to the second position is preferably the same as a direction in which the second wire is wound around the outer side of the insertion member from the second position to the third position.

A direction in which the first wire is wound around the outer side of the insertion member from the first position to the second position may be opposite to the direction in which the second wire is wound around the outer side of the insertion member from the second position to the third position.

The first side hole and the second side hole are preferably located at positions overlapping with each other in a circumferential direction of the shaft.

The first side hole and the second side hole are preferably located at positions not overlapping with each other in a circumferential direction of the shaft.

The shaft, the insertion member, and the first wire are preferably fixed to each other on a proximal side of the second side hole.

A gist of still another embodiment of a catheter of the present invention is to include: a shaft having a distal end and a proximal end in a longitudinal axis direction, the shaft having a fourth side hole provided on a wall of the shaft and a lumen extending in the longitudinal axis direction; an insertion member disposed in the lumen of the shaft; a fourth electrode provided on an outer side of the fourth side hole; a fourth wire that is electrically connected to the fourth electrode and extends through the fourth side hole to an outer side of the insertion member in the lumen of the shaft; and a fixed part in which the shaft, the insertion member, and the fourth wire are fixed to each other on a proximal side of the fourth side hole, wherein the fourth wire has a fourth position and a fifth position inside the shaft, the fourth position being located at a same position as the fourth side hole in the longitudinal axis direction, and the fifth position being located at a same position as the fixed part in the longitudinal axis direction, and the fifth position of the fourth wire is located at a position deviated from the fourth position by 90 degrees or more in a circumferential direction of the insertion member. According to the catheter, since the fourth wire is disposed such that the fifth position is located at the position deviated from the fourth position by 90 degrees or more in the circumferential direction of the insertion member, it is possible to provide a margin for a length of the fourth wire in the lumen of the shaft. Thus, even if the fourth wire is dragged due to the curving of the shaft, such dragging can be absorbed by the extra length, so that the fourth wire can be prevented from propping up. Therefore, the flexibility of the distal end portion of the catheter can be secured.

The fourth side hole is preferably located on the proximal side of a central position of a length from the distal end of the shaft to a distal end of the fixed part in the longitudinal axis direction of the shaft.

The fourth wire is preferably wound around the outer side of the insertion member from the fourth position to the fifth position.

It is preferable that the insertion member has: a cylinder member having a distal end and a proximal end in a longitudinal axis direction, the cylinder member having a lumen extending in the longitudinal axis direction; and an elastic member disposed in the lumen of the cylinder member, an outer shape of a cross section perpendicular to the longitudinal axis direction of the cylinder member is an ellipse having a long diameter and a short diameter, and the first side hole or the fourth side hole is disposed to face a portion of the short diameter of the ellipse of the cylinder member.

The shaft is preferably capable of curving in two directions, that is, a normal direction of the first side hole or the fourth side hole and a direction opposite to the normal direction.

The present invention also provides a method for manufacturing a catheter. A method for manufacturing a catheter, the method comprising: a step of preparing a shaft having a distal end and a proximal end in a longitudinal axis direction, the shaft having a first side hole on a wall of the shaft and a lumen extending in the longitudinal axis direction; a step of inserting a first wire into the lumen of the shaft through the first side hole to expose the first wire from the proximal end of the shaft; a step of inserting an insertion member into the lumen of the shaft; a step of pulling the first wire in a state where the shaft is curved; and a step of releasing the curving of the shaft. Since the method for manufacturing the catheter includes the step of pulling the first wire in a state where the shaft is curved and the step of releasing the curving of the shaft in order, it is possible to provide a margin for a length of the first wire in the lumen of the shaft. Thus, even if the first wire is dragged due to the curving of the shaft during the operation, such dragging can be absorbed by the extra length, so that the prop-up of the first wire can be prevented. Therefore, the flexibility of the distal end portion of the catheter can be secured.

It is preferable that, in step of preparing the shaft, the shaft be provided with a second side hole on the wall of the shaft on a proximal side of the first side hole, the first side hole and the second side hole being located at positions overlapping with each other in a circumferential direction of the shaft, and that the first side hole and the second side hole be disposed on an outer side a curve in the step of pulling the first wire.

It is preferable that the shaft be provided with a second side hole on the wall of the shaft on a proximal side of the first side hole in step of preparing the shaft, that a step of inserting a second wire into the lumen of the shaft through a second side hole to expose the second wire from the proximal end of the shaft be further provided before the step of inserting the insertion member into the lumen of the shaft, and that the second wire be also pulled in the step of pulling the first wire.

It is preferable to further provide a step of fixing the shaft, the first wire, and the insertion member to each other on the proximal side of the first side hole after step of releasing the curving of the shaft.

It is preferable to further provide a step of fixing the shaft, the first wire, and the insertion member to each other on the proximal side of the first side hole before step of releasing the curving of the shaft and after the step of pulling the first wire.

Effects of the Invention

According to the catheter and the method for manufacturing the catheter, it is possible to provide the margin for the length of the wire in the lumen of the shaft. Thus, even if the wire is dragged due to the curving of the shaft during the operation, such dragging can be absorbed by the extra length, so that the prop-up of the wire can be prevented. Therefore, the flexibility of the distal end portion of the catheter can be secured.

BRIEF DESCRIPTION OF THE DRAWINGS

FIG. 1 illustrates a side view of a catheter according to one embodiment of the present invention.

FIG. 2 illustrates side cross-sectional view of the catheter taken along line II-II of FIG. 1.

FIG. 3 illustrates side cross-sectional view of the catheter taken along line III-III of FIG. 1.

FIG. 4 illustrates cross-sectional view of the catheter taken along line IV-IV of FIG. 2.

FIG. 5 illustrates cross-sectional view of the catheter taken along line V-V of FIG. 2.

FIG. 6 illustrates cross-sectional view of the catheter taken along line VI-VI of FIG. 2.

FIG. 7 illustrates a cross-sectional view of a catheter illustrating a modification of FIG. 4.

FIG. 8 is a side cross-sectional view illustrating a modification of the catheter illustrated in FIG. 2.

FIG. 9 illustrates perspective view of the distal end portion of the shaft of FIG. 1.

FIG. 10 illustrates perspective view of the shaft illustrating a modification of FIG. 9.

FIG. 11 illustrates a side cross-sectional view of a conventional catheter along a longitudinal axis direction of the conventional catheter.

DESCRIPTION OF EMBODIMENTS

The present invention will be specifically explained below based on the following embodiments, however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

1. Catheter

A catheter is used, for example, for diagnosis and treatment of arrhythmia. In the diagnosis of arrhythmia, an electrocardiogram can be obtained by inserting the catheter into a body of a patient, disposing an electrode in or near a tissue to be diagnosed of a heart, and measuring a potential of the tissue. In addition, in the treatment of arrhythmia, for example, a body tissue can be cauterized by applying a high-frequency current to the electrode of the catheter.

A gist of one embodiment of a catheter of the present invention is to include: a shaft having a distal end and a proximal end in a longitudinal axis direction and a lumen extending in the longitudinal axis direction, the shaft having a wall having a first side hole and a second side hole provided adjacently in order from a distal side; an insertion member disposed in the lumen of the shaft; a first electrode provided on the outer side of the first side hole; and a first wire that is electrically connected to the first electrode and extends through the first side hole to the outer side of the insertion member in the lumen of the shaft, the first wire having a first position and a second position inside the shaft, the first position being located at the same position as the first side hole in the longitudinal axis direction of the shaft, the second position being located at the same position as the second side hole in the longitudinal axis direction of the shaft, and the second position of the first wire being located at a position deviated from the first position by 45 degrees or more in a circumferential direction of the insertion member. According to the catheter, since the first wire is disposed such that the second position is located at the position deviated from the first position by 45 degrees or more in the circumferential direction of the insertion member, it is possible to provide a margin for a length of the first wire in the lumen of the shaft. Thus, even if the first wire is dragged due to the curving of the shaft, such dragging can be absorbed by the extra length, so that the first wire can be prevented from propping up. Therefore, the flexibility of the distal end portion of the catheter can be secured. In the following description, such an aspect will be referred to as a first embodiment.

A conventional catheter has the following problems. In a case where the catheter, made of a flexible material, in a straight state is curved into a curved state, a length of a path of a shaft wall of the catheter is shortened on the inner side of the curve, and a length of the path is extended on the outer side of the curve. The catheter is curved in a case of being provided with a curving mechanism or in a case of following a curve in a body cavity. Since the shaft wall of the flexible catheter has elasticity, a shape thereof can be changed following a change in a shape of the catheter. Meanwhile, a wire is made of metal, and thus, lacks elasticity and is not able to follow a change in the shape of the catheter. In a case where the wire is disposed close to an inner wall surface of the shaft of the catheter, the wire is not able to stretch but tends to move toward the inner side of the curve if the inner wall surface is disposed on the outer side of the curve, so that the catheter fails to obtain a planned curved shape or is not curved. In order to prevent such a defect, the wire needs to have a margin. However, the lumen of the shaft of the catheter has a limited size, and it has been difficult to dispose the wire in the lumen beyond a length of the lumen of the catheter in the straight state due to a difficulty in manufacturing. On the other hand, in the catheter according to the first embodiment of the present invention in which the first wire is at a position deviated from the first position to the second position by 45 degrees or more in the circumferential direction, the length of the wire disposed between the first position and the second position is longer than that of a catheter in which a first wire is disposed straight from a first position to a second position. Thus, it is possible to provide a margin for the length of the first wire in the lumen of the shaft.

A gist of another embodiment of a catheter of the present invention is to include: a shaft having a distal end and a proximal end in a longitudinal axis direction and a lumen extending in the longitudinal axis direction, the shaft having a wall having a first side hole, a second side hole, and a third side hole provided adjacently in order from a distal side; an insertion member disposed in the lumen of the shaft; a first electrode provided on the outer side of the first side hole; and a first wire that is electrically connected to the first electrode and extends through the first side hole to the outer side of the insertion member in the lumen of the shaft, the first wire having a first position, a second position, and a third position inside the shaft, the first position being located at the same position as the first side hole in the longitudinal axis direction of the shaft, the second position being located at the same position as the second side hole in the longitudinal axis direction of the shaft, the third position being located at the same position as the third side hole in the longitudinal axis direction of the shaft, and the third position of the first wire being located at a position deviated from the first position by 90 degrees or more in a circumferential direction of the insertion member. According to the catheter, since the first wire is disposed such that the third position is located at the position deviated from the first position by 90 degrees or more in the circumferential direction of the insertion member, it is possible to provide a margin for a length of the first wire in the lumen of the shaft. Thus, even if the first wire is dragged due to the curving of the shaft, such dragging can be absorbed by the extra length, so that the first wire can be prevented from propping up. Therefore, the flexibility of the distal end portion of the catheter can be secured. In the following description, such an aspect will be referred to as a second embodiment.

A gist of still another embodiment of a catheter of the present invention is to include: a shaft having a distal end and a proximal end in a longitudinal axis direction, the shaft having a fourth side hole provided on a wall of the shaft and a lumen extending in the longitudinal axis direction; an insertion member disposed in the lumen of the shaft; a fourth electrode provided on the outer side of the fourth side hole; a fourth wire that is electrically connected to the fourth electrode and extends through the fourth side hole to the outer side of the insertion member in the lumen of the shaft; and a fixed part in which the shaft, the insertion member, and the fourth wire are fixed to each other on a proximal side of the fourth side hole, the fourth wire having a fourth position and a fifth position inside the shaft, the fourth position being located at the same position as the fourth side hole in the longitudinal axis direction of the shaft, the fifth position being located at the same position as the fixed part in the longitudinal axis direction of the shaft, and the fifth position of the fourth wire being located at a position deviated from the fourth position by 90 degrees or more in a circumferential direction of the insertion member. According to the catheter, since the fourth wire is disposed such that the fifth position is located at the position deviated from the fourth position by 90 degrees or more in the circumferential direction of the insertion member, it is possible to provide a margin for a length of the fourth wire in the lumen of the shaft. Thus, even if the fourth wire is dragged due to the curving of the shaft, such dragging can be absorbed by the extra length, so that the fourth wire can be prevented from propping up. Therefore, the flexibility of the distal end portion of the catheter can be secured. In the following description, such an aspect will be referred to as a third embodiment.

A configuration example of a catheter will be described with reference to FIGS. 1 to 8. FIG. 1 illustrates a side view of a catheter according to one embodiment of the present invention, and FIGS. 2 to 3 illustrate side cross-sectional views of the catheter taken along lines II-II and III-III of FIG. 1, respectively. FIGS. 4 to 6 illustrate cross-sectional views of the catheter taken along lines IV-IV, V-V, and VI-VI of FIG. 2, respectively. FIG. 7 illustrates a cross-sectional view of a catheter illustrating a modification of FIG. 4. FIG. 8 is a side cross-sectional view illustrating a modification of the catheter illustrated in FIG. 2. Note that FIGS. 4 to 7 illustrates only a first wire 51 among wires 50, and does not illustrate a second wire 52 and a third wire 53 in order to contribute to understanding of the present invention.

In a catheter 1, a distal side refers to a distal end side in a longitudinal axis direction x of a shaft 10 and a treatment target side. In addition, a proximal side refers to a proximal end side in the longitudinal axis direction x of the shaft 10 and a hand side of a user (operator). When each member is divided into two equal parts in its longitudinal axis direction, the proximal side may be referred to as a proximal portion, and the distal side may be referred to as a distal portion. In FIG. 1, a left side represents the distal side, and a right side represents the proximal side. The inside of the catheter 1 refers to a direction toward a longitudinal-axis center of the shaft 10 in a radial direction of the shaft 10, and the outside refers to a radial direction opposite to the inside.

The shaft 10 is a member having a distal end and a proximal end in the longitudinal axis direction, and a distal end side thereof is inserted into a body of a patient. The shaft 10 has a lumen 11 extending in the longitudinal axis direction x. The shaft 10 preferably has a cylindrical structure in order to dispose the wires 50 the lumen 11. In addition, the shaft 10 is inserted into the body, and thus, preferably has flexibility. As the shaft 10 having the cylindrical structure, a hollow coil formed by spirally winding one or a plurality of metal wire materials, what is obtained by coating at least one of an inner surface and an outer surface of the hollow coil or a hollow body with a resin, a cylindrical resin tube, or what is obtained by connecting these in the longitudinal axis direction x may be used. When the shaft 10 is the cylindrical resin tube, the shaft 10 can include a single layer or a plurality of layers, and may have a part in the longitudinal axis direction x or a circumferential direction including a single layer, and the other part including a plurality of layers. Although not illustrated, a plurality of the lumens 11 of the shaft 10 may be provided. As illustrated in FIG. 1, an operation part 70, gripped by the operator, is preferably connected to a proximal portion of the shaft 10. In addition, a tip 17 is preferably disposed in a distal end portion of the shaft 10. The tip 17 may be an electrode or may be a resin member configured to block an opening on the distal side of the shaft 10. Regarding a material forming the tip 17, a description on a material forming the shaft 10 to be described later can be referred to.

The shaft 10 can be made of, for example, a synthetic resin, such as a polyolefin resin (for example, polyethylene or polypropylene), a polyamide resin (for example, nylon), a polyester resin (for example, PET), an aromatic polyether ketone resin (for example, PEEK), a polyether polyamide resin, a polyurethane resin, a polyimide resin, and a fluororesin (for example, PTFE, PFA, or ETFE), or metal such as stainless steel, carbon steel, or a nickel-titanium alloy. Only one kind of them may be used singly, or two or more kinds of them may be used in combination.

Although not illustrated, a reinforcing member made of metal may be disposed in the shaft 10. The reinforcing member may be formed in a layer shape, or may be formed by disposing or braiding a single wire or a stranded wire material in a specific pattern. As a result, the strength and torque of the shaft 10 can be enhanced. A shape of a cross section of the wire material may be, for example, a circular shape, an oval shape, a polygonal shape, or a shape obtained by combining these shapes. The oval shape includes an elliptical shape, an egg shape, and a rounded rectangular shape. The same also applies to the following description. Note that, regarding a material forming the reinforcing member, the description on the metal forming the shaft 10 can be referred to. The reinforcing member can be disposed on an outer surface or an inner surface of the shaft 10, or inside a wall 12.

The shaft 10 can be curved. The shaft 10 is preferably curved two-dimensionally, but may be three-dimensionally curved. Here, the two-dimensional curving of the shaft 10 means that a distal end and a proximal end of a curved portion of the shaft are located on the substantially same plane before and after the curving. FIG. 1 illustrates an example in which a distal portion of the shaft 10 can curve in two directions of a direction A and a direction B opposite to the direction A. The three-dimensional curving means that a plane on which a distal end and a proximal end of a curved portion of the shaft are located before the curving is different from a plane on which the distal end and the proximal end are located after the curving. That is, the three-dimensional curving means that the shaft is twisted by the curving.

The wall 12 (preferably a peripheral wall) of the shaft 10 has side holes 30. As a result, the wires 50 can be inserted into the lumen 11 of the shaft 10 through the side hole 30. The side holes 30 are provided so as to penetrate from the outside of the shaft 10 to the lumen 11. As illustrated in FIG. 2, the wall 12 of the shaft 10 of the catheter 1 according to the first embodiment has a first side hole 31 and a second side hole 32 provided adjacently in order from the distal side. In addition, as illustrated in FIG. 2, the wall 12 of the shaft 10 of the catheter 1 according to the second embodiment has the first side hole 31, the second side hole 32, and a third side hole 33 provided adjacently in order from the distal side. In addition, as illustrated in FIG. 3, a fourth side hole 34 is provided on the wall 12 of the shaft 10 of the catheter 1 according to the third embodiment.

In the respective embodiments, the wall 12 of the shaft 10 can have one or a plurality of the side holes 30 other than the first side hole 31 to the third side hole 33. The total number of the side holes 30 of the shaft 10 is not particularly limited, but is preferably 2 or more, more preferably 3 or more, even more preferably 5 or more, and still even more preferably 10 or more and may also be allowed to be 30 or less, 25 or less, or 20 or less. Note that a fifth side hole 35 is further provided on the proximal side of the fourth side hole 34 in FIG. 3.

A shape of the side hole 30 can be a circular shape, an oval shape, a polygonal shape, or a combination thereof. The side hole 30 may be provided so as to have a central axis coinciding with a radial direction of the shaft 10, or may be provided so as to have the central axis extending from the outside to the inside in the radial direction as proceeding from the distal side to the proximal side of the shaft 10.

Each of electrodes 40 is provided on the outer side of each of the side holes 30 of the shaft 10. The electrode 40 functions as a measurement electrode or a reference electrode (for example, a ground electrode) at the time of potential measurement. In the catheters 1 according to the first and second embodiments, a first electrode 41 is provided on the outer side of the first side hole 31. In addition, a fourth electrode 44 is provided on the outer side of the fourth side hole 34 in the catheter 1 according to the third embodiment. In addition to the above, a second electrode 42 and a third electrode 43 are provided on the outer side of the second side hole 32 and on the outer side of the third side hole 33, respectively, in FIG. 2, and a fifth electrode 45 is provided on the outer side of a fifth side hole 35 (the proximal-most side hole 30) in FIG. 3.

The total number of the electrodes 40 is not particularly limited, but it is preferable that each of the electrodes 40 be disposed on the outer side of each of all the side holes 30 provided in the shaft 10.

Examples of a shape of the electrode 40 include a ring shape, a shape having a C-shaped cross section obtained by forming a notch in a ring, and a coil shape obtained by winding a wire material. The electrode 40 can be disposed on the shaft 10 by caulking the electrode 40 to the shaft 10.

The electrode 40 only needs to have conductivity, and can be made of metal or a mixture containing resin and metal. Among them, it is preferable to use metal, such as a conductive resin, platinum, a platinum iridium alloy, stainless steel, and tungsten, as a material of the electrode 40. In a case where the electrode 40 is made of a conductive resin, it is preferable to mix a contrast medium, such as barium sulfate and bismuth oxide, in order for visibility under X-ray fluoroscopy.

The wire 50 electrically connects the electrode 40 and an external device of the catheter 1, for example, an electrocardiograph. The wire 50 is electrically connected to the electrode 40 and extends through the side hole 30 to the outer side of the insertion member 20 in the lumen 11 of the shaft 10. As illustrated in FIG. 2, in the catheters 1 according to the first and second embodiments, the first wire 51 is electrically connected to the first electrode 41, and extends through the first side hole 31 to the outer side of the insertion member 20 in the lumen 11 of the shaft 10. As illustrated in FIG. 3, in the catheter 1 according to the third embodiment, the fourth wire 54 is electrically connected to the fourth electrode 44, and extends through the fourth side hole 34 to the outer side of the insertion member 20 in the lumen 11 of the shaft 10. In addition to the above, in FIG. 2, the second wire 52 is electrically connected to the second electrode 42, and extends through the second side hole 32 to the outer side of the insertion member 20 in the lumen 11 of the shaft 10, and the third wire 53 is electrically connected to the third electrode 43, and extends through the third side hole 33 to the outer side of the insertion member 20 in the lumen 11 of the shaft 10. In addition, in FIG. 3, the fifth wire 55 is electrically connected to the fifth electrode 45, and extends through the fifth side hole 35 to the outer side of the insertion member 20 in the lumen 11 of the shaft 10.

The wire 50 only needs to have conductivity, and for example, a copper wire, an iron wire, a stainless steel wire, a piano wire, a tungsten wire, a nickel titanium wire, or the like can be used. In the wire 50, a portion other than both end portions in the longitudinal axis direction may be covered with a covering member such as a covering tube. As a result, it is possible to prevent a short circuit with an adjacent member. Regarding a material of the covering member of the wire 50, the description on the resin material forming the shaft 10 can be referred to.

The electrode 40 and the wire 50 can be connected by a method such as laser welding, resistance welding, and adhesion with an adhesive.

The insertion member 20 is a member disposed in the lumen 11 of the shaft 10. Since the insertion member 20 is disposed inside the shaft 10, it is possible to retain a shape of the distal end portion of the shaft 10 during an operation or to curve the distal end portion of the shaft 10 during the operation.

As illustrated in FIG. 4, the insertion member 20 preferably includes a cylinder member 21 having a distal end and a proximal end in a longitudinal axis direction, the cylinder member 21 having a lumen extending in the longitudinal axis direction, and an elastic member 22 disposed in the lumen of the cylinder member 21. As a result, the degree of curvature of the distal portion of the shaft 10 can be finely adjusted, and thus, the operation can be appropriately performed.

The cylinder member 21 is provided to accommodate an operation wire 25, which will be described later, the elastic member 22, and the like, whereby it is possible to prevent the operation wire 25 and the elastic member 22 from coming into contact with the wire 50. The cylinder member 21 may extend in the longitudinal axis direction x of the shaft 10. As the cylinder member 21, a resin tube, a cylindrical body formed by disposing a single wire or a plurality of wire materials, or a stranded wire material in a specific pattern, a metal tube, or a combination thereof can be used, which is similar to the shaft 10. The cylinder member 21 can be made of the resin or metal described as the material forming the shaft 10. The material of the cylinder member 21 may be the same as or different from the material of the shaft 10.

An outer shape of a cross section perpendicular to the longitudinal axis direction of the cylinder member 21 is not particularly limited, and can be a circular shape, an oval shape, a polygonal shape, or a shape obtained by combining these. Among them, an elliptical shape having a short diameter 21A and a long diameter 21B as illustrated in FIG. 7 is preferable. As a result, it is easy to secure a space for disposing the wire 50 outside a portion with the short diameter 21A of the ellipse of the cylinder member 21 in the lumen 11 of the shaft 10.

As illustrated in FIG. 4, the lumen 11 of the shaft 10 is preferably provided with the operation wire 25 extending in the longitudinal axis direction x of the shaft 10. The number of the operation wires 25 disposed in the lumen 11 of the shaft 10 may be one or plural. The distal portion of the shaft 10 can be curved by pulling the operation wire 25 to the proximal side. Alternatively, the distal portion of the shaft 10 may be curved by pushing the operation wire 25 to the distal side. A distal portion of the operation wire 25 is fixed to a distal portion of the catheter 1, preferably a distal portion of the elastic member 22, which will be described later, and a proximal portion of the operation wire 25 is fixed to the operation part 70.

As the operation wire 25, for example, a metal wire material, such as stainless steel, carbon steel, and a nickel titanium alloy, or a strand made of a synthetic resin such as a polyamide resin (for example, nylon), a polyolefin resin (for example, polyethylene or polypropylene), a polyester resin (for example, PET), an aromatic polyether ketone resin (for example, PEEK), a polyimide resin, and a fluororesin (for example, PTFE, PFA, FEP, or ETFE) can be used.

The elastic member 22 is provided to enable the degree of curving of the distal portion of the shaft 10 to be finely adjusted. The elastic member 22 preferably extends along the longitudinal axis direction of the cylinder member 21. Examples of the elastic member 22 can include a leaf spring and a coil spring, but the leaf spring is preferable as illustrated in FIGS. 4 to 7 in consideration of the arrangement in the cylinder member 21. The leaf spring is disposed so as to have a longitudinal axis direction extending along the longitudinal axis direction of the cylinder member 21, for example. In that case, a distal portion of the leaf spring can be fixed to the distal portion (preferably, the tip 17) of the shaft 10. A method for joining the elastic member 22 and the shaft 10 or the tip 17 is not particularly limited, and methods, such as brazing such as solder, welding, adhesion with an adhesive, and caulking, may be used. As a material forming the elastic member 22, the description on the material forming the operation wire 25 can be referred to.

It is preferable to dispose the operation wire 25 in the lumen of the cylinder member 21 and to fix the distal end portion of the operation wire 25 to the distal portion of the elastic member 22. Since the insertion member 20 can be curved and released from curving by the operation wire 25 and the elastic member 22, the shaft 10 can be curved and released accompanying the curving and the release of curving of the operation wire 25. Note that the operation wire 25 is preferably disposed so as to be eccentric from a longitudinal-axis center of the cylinder member 21. For example, in a case where the elastic member 22 is a leaf spring, the operation wire 25 can be disposed on one major surface side of the leaf spring.

The catheter according to the first embodiment will be described in detail. As illustrated in FIG. 2, in the shaft 10, the first wire 51 has: a first position 61 located at the same position as the first side hole 31 in the longitudinal axis direction x of the shaft 10; and a second position 62 located at the same position as the second side hole 32 in the longitudinal axis direction x of the shaft 10. The second position 62 of the first wire 51 is located at a position deviated from the first position 61 by 45 degrees or more in the circumferential direction of the insertion member 20. According to the catheter 1, since the first wire 51 is disposed such that the second position 62 is located at the position deviated from the first position 61 by 45 degrees or more in the circumferential direction of the insertion member 20, it is possible to provide a margin for a length of the first wire 51 in the lumen 11 of the shaft 10. Thus, even if the first wire 51 is dragged due to the curving of the shaft 10, such dragging can be absorbed by the extra length, so that the first wire 51 can be prevented from propping up. Therefore, the flexibility of a distal end portion of the catheter 1 can be secured.

The first position 61, located at the same position as the first side hole 31 in the longitudinal axis direction x of the shaft 10, refers to a range from a distal end to a proximal end of the first side hole 31 in the longitudinal axis direction x of the shaft 10. Note that the second position 62, the third position 63, and the fourth position 64 are also similarly defined.

In order to contribute to the understanding of the present invention, FIG. 2 illustrates a straight line L1, which is parallel to the longitudinal axis direction x and indicates a position deviated from a distal-most position of the longitudinal-axis center of the first wire 51 by 45 degrees in the circumferential direction of the insertion member 20 in the first position 61, and a straight line L2 which is parallel to the longitudinal axis direction x and indicates a position deviated from the distal-most position by 90 degrees in the circumferential direction of the insertion member 20.

As illustrated in FIGS. 2 and 5, the second position 62 of the first wire 51 only needs to be at a position deviated from the first position 61 by 45 degrees or more in the circumferential direction of the insertion member 20, and is at a position deviated by preferably 60 degrees or more, more preferably 70 degrees or more, even more preferably 90 degrees or more, and still even more preferably 120 degrees or more. As a result, it is possible to appropriately provide a margin for the length of the first wire 51 in the lumen 11 of the shaft 10. Note that, in FIG. 5, the deviation of the second position 62 from the first position 61 (in detail, a deviation of a proximal-most position of the second position 62 from the distal-most position of the longitudinal-axis center of the first wire 51 in the first position 61) is represented by an angle θ1.

The second position 62 of the first wire 51 is preferably located at the position deviated from the first position 61 by 270 degree or less in the circumferential direction of the insertion member 20, and is at a position deviated by more preferably 240 degree or less, even more preferably 200 degree or less, and still even more preferably 180 degree or less. As a result, it is possible to prevent entanglement of the wires 50 due to excessive slackening of the wires 50 in the lumen 11 of the shaft 10.

Next, the catheter 1 according to the second embodiment will be described in detail. Note that the catheter 1 according to the second embodiment will be described with reference to FIG. 2 similarly to the catheter 1 according to the first embodiment, but the catheter 1 according to the second embodiment may have the configuration of the catheter 1 according to the first embodiment, but does not necessarily have the configuration.

As illustrated in FIG. 2, in the shaft 10, the first wire 51 has: the first position 61 located at the same position as the first side hole 31 in the longitudinal axis direction x of the shaft 10; the second position 62 located at the same position as the second side hole 32 in the longitudinal axis direction x of the shaft 10; and a third position 63 located at the same position as the third side hole 33 in the longitudinal axis direction x of the shaft 10. The third position 63 of the first wire 51 is located at a position deviated from the first position 61 by 90 degrees or more in the circumferential direction of the insertion member 20. According to the catheter 1, since the first wire 51 is disposed such that the third position 63 is located at the position deviated from the first position 61 by 90 degree or more in the circumferential direction of the insertion member 20, it is possible to provide a margin for a length of the first wire 51 in the lumen 11 of the shaft 10. Thus, even if the first wire 51 is dragged due to the curving of the shaft 10, such dragging can be absorbed by the extra length, so that the first wire 51 can be prevented from propping up. Therefore, the flexibility of a distal end portion of the catheter 1 can be secured.

As illustrated in FIGS. 2 and 6, the third position 63 of the first wire 51 only needs to be at a position deviated from the first position 61 by 90 degrees or more in the circumferential direction of the insertion member 20, and is at a position deviated by preferably 100 degrees or more, more preferably 120 degrees or more, even more preferably 140 degrees or more, and still even more preferably 160 degrees or more. As a result, it is possible to appropriately provide a margin for the length of the first wire 51 in the lumen 11 of the shaft 10. Note that, in FIG. 6, the deviation of the third position 63 from the first position 61 (in detail, a deviation of a proximal-most position of the third position 63 from the distal-most position of the longitudinal-axis center of the first wire 51 in the first position 61) is represented by an angle θ2. Note that the angle θ2 is preferably larger than the angle θ1.

The third position 63 of the first wire 51 is preferably located at the position deviated from the first position 61 by 270 degree or less in the circumferential direction of the insertion member 20, and is at a position deviated by more preferably 240 degree or less, even more preferably 200 degree or less, and still even more preferably 180 degree or less. As a result, it is possible to prevent entanglement of the wires 50 due to excessive slackening of the wires 50 in the lumen 11 of the shaft 10.

Hereinafter, matters common to the catheters 1 according to the first and second embodiments will be described.

In the catheter 1 according to the first embodiment, any side hole 30 may correspond to the first side hole 31 except for the side hole 30 located on the most proximal side. In addition, in the catheter 1 according to the second embodiment, any side hole 30 may correspond to the first side hole 31 except for the side hole 30 located on the most proximal side and the side hole 30 which is the second counted from the proximal side. That is, the first side hole 31 may be the side hole 30 disposed most distantly in the shaft 10, and the first side hole 31 may be the second or subsequent side hole 30 counted from the distal side of the shaft 10.

In the longitudinal axis direction x of the shaft 10, a first distance from the proximal end of the first side hole 31 to the distal end of the second side hole 32 is not particularly limited, but is preferably wider than a width of the first electrode 41 in order to prevent contact between the adjacent electrodes 40.

In the longitudinal axis direction x of the shaft 10, a second distance from the proximal end of the second side hole 32 to the distal end of the third side hole 33 is preferably wider than the first distance from the proximal end of the first side hole 31 to the distal end of the second side hole 32. As a result, a distance between the electrodes 40 can be narrowed as proceeding to the distal side of the shaft 10. Note that the first distance and the second distance may be the same.

The first wire 51 is preferably wound around the outer side of the insertion member 20 from the first position 61 to the second position 62. Such winding around the outer side of the insertion member 20 makes it easy to provide the margin for the length of the first wire 51 in the lumen 11 of the shaft 10.

The wire 50 being wound around the outer side of the insertion member 20 is not limited to an aspect of being wound around the outer periphery of the insertion member 20 one turn or more, and also includes an aspect of extending one turn or less, for example, half turn or less, or quarter turn or less.

The first wire 51 is preferably wound spirally. As a result, it is easy to provide the margin for the length of the first wire 51 in the lumen 11 of the shaft 10 while preventing a kink of the first wire 51.

Although not illustrated, at least a part of the first wire 51, preferably at least a part from the first position 61 to the second position 62 may be formed in a wave shape. It is possible to provide the margin for the length of the first wire 51 by extending the first wire 51 in this manner. Although not illustrated, at least a part of the first wire 51, preferably at least a part from the first position 61 to the second position 62 may be in contact with an inner wall of the shaft 10. It is possible to provide the margin for the length of the first wire 51 by making the first wire 51 to follow the inner wall of the shaft 10 in this manner.

The first wire 51 is preferably formed not to be bent but to be curved from the first position 61 to the second position 62. In other words, the first wire 51 preferably does not have a bent portion at least from the first position 61 to the second position 62, and more preferably does not have the bent portion over the entire first wire 51. As a result, it is possible to provide the margin for the length of the first wire 51 in the lumen 11 of the shaft 10 while preventing a kink of the first wire 51. Specifically, it is preferable that the first wire 51 not have a bent portion that is bent at a substantially right angle.

The catheter 1 may further include the second electrode 42 provided on the outer side of the second side hole 32 and the second wire 52 that is electrically connected to the second electrode 42 and extends through the second side hole 32 to the outer side of the insertion member 20 in the lumen 11 of the shaft 10. In this case, it is preferable that the third side hole 33 be provided on the wall 12 of the shaft 10 on the proximal side of the second side hole 32, that the second wire 52 have, in the shaft 10, the second position 62 located at the same position as the second side hole 32 in the longitudinal axis direction x of the shaft 10 and the third position 63 located at the same position as the third side hole 33 in the longitudinal axis direction x of the shaft 10, and that the third position 63 of the second wire 52 be located at a position deviated from the second position 62 by 45 degrees or more in the circumferential direction of the insertion member 20. According to the catheter 1, since the second wire 52 is disposed such that the third position 63 is located at the position deviated from the second position 62 by 45 degrees or more in the circumferential direction of the insertion member 20, it is possible to provide a margin for a length of the second wire 52 in the lumen 11 of the shaft 10. Thus, even if the second wire 52 is dragged due to the curving of the shaft 10, such dragging can be absorbed by the extra length, so that the second wire 52 can be prevented from propping up. Therefore, the flexibility of a distal end portion of the catheter 1 can be secured.

In the circumferential direction of the insertion member 20, the third position 63 of the second wire 52 can be located at a position deviated from the second position 62 by, for example, 60 degree or more, 90 degree or more, or 120 degree or more, or alternatively, 270 degree or less, 240 degree or less, 200 degree or less, or 180 degree or less.

Winding directions of the plurality of wires 50 are not particularly limited, and winding directions of one wire 50 and the other wire 50 may be the same or different from each other. In addition, the winding directions of all the wires 50 provided in the catheter 1 may be the same.

As illustrated in FIG. 2, a direction in which the first wire 51 is wound around the outer side of the insertion member 20 from the first position 61 to the second position 62 is preferably the same as a direction in which the second wire 52 is wound around the outer side of the insertion member 20 from the second position 62 to the third position 63. When the arrangement directions of the adjacent wires 50 are the same, the wires 50 can be disposed with a high accuracy, and the entanglement of the wires 50 can be prevented.

As illustrated in FIG. 8, the direction in which the first wire 51 is wound around the outer side of the insertion member 20 from the first position 61 to the second position 62 may be opposite to the direction in which the second wire 52 is wound around the outer side of the insertion member 20 from the second position 62 to the third position 63. When the arrangement direction is changed between the adjacent wires 50 in this manner, it is possible to enhance the effect of preventing the entanglement of the wires 50 in the distal portion of the shaft 10.

In a case where the plurality of electrodes 40 provided on the shaft 10 are divided into a distal-side electrode group, which is located in the distal portion of the shaft 10 and includes at least two electrodes 40, and a proximal-side electrode group which is located in the proximal portion of the shaft 10 and includes at least two electrodes 40, the wires 50 connected to the distal-side electrode group may be wound in the same direction, and the wires 50 connected to the proximal-side electrode group may be wound in the same direction. In addition, the winding direction of the wires 50 connected to the distal-side electrode group and the winding direction of the wires 50 connected to the proximal-side electrode group may be the same or different from each other.

The position of the side hole 30 of the shaft 10 is not particularly limited, and can be disposed, for example, as follows. FIGS. 9 to 10 represent perspective views of the distal end portion of the shaft 10, and illustrate arrangement examples of the plurality of side holes 30.

As illustrated in FIG. 9, the first side hole 31 and the second side hole 32 are preferably located at positions overlapping with each other in a circumferential direction of the shaft 10. As a result, it is easy to adjust an extending direction of the wire 50 so as to have the extra length at the time of manufacturing the catheter 1. When the shaft 10 is viewed from the distal end side, at least a part of the first side hole 31 and at least a part of the second side hole 32 are preferably located at positions overlapping with each other, and a central position of the first side hole 31 and a central position of the second side hole 32 preferably coincide with each other in the circumferential direction of the shaft 10.

All the side holes 30 provided in the shaft 10 may be located at positions overlapping with each other in the circumferential direction of the shaft 10. As a result, it is possible to adjust the extending directions of all the wires 50 so as to have the extra length at the time of manufacturing the catheter 1.

As illustrated in FIG. 10, the first side hole 31 and the second side hole 32 are preferably located at positions not overlapping with each other in a circumferential direction of the shaft 10. As a result, the first wire 51 and the second wire 52 are easily disposed so as to be deviated from each other in the circumferential direction, and thus, it is possible to prevent the entanglement of the wires 50.

When the shaft 10 is viewed from the distal side, the center of the second side hole 32 is preferably located at a position deviated from the center of the first side hole 31, in the circumferential direction of the shaft 10, by 5 degrees or more, preferably 10 degrees or more, more preferably 20 degrees or more, and even more preferably 30 degrees or more, and may also be allowed to be deviated by 90 degrees or less, 80 degrees or less, or 60 degrees or less.

The shaft 10, the insertion member 20, and the first wire 51 are preferably fixed to each other on the proximal side of the second side hole 32. As a result, an operating direction of the shaft 10 is regulated, and thus, the shaft 10 can be curved with a fixed part as a base point. In addition, such a fixing enables the shaft 10 which is easily curved two-dimensionally, and it is possible to prevent the three-dimensional curving of the shaft 10. The shaft 10, the insertion member 20, and the first wire 51 are preferably fixed at a fixed part 15 to be described later.

Next, the catheter according to the third embodiment will be described in detail. Note that the catheter according to the third embodiment may simultaneously include at least one aspect of the first and second embodiments.

As illustrated in FIG. 3, the catheter 1 according to the third embodiment include: the shaft 10 having the distal end and the proximal end in the longitudinal axis direction x, the shaft 10 having the fourth side hole 34 provided on the wall 12 of the shaft 10 and the lumen 11 extending in the longitudinal axis direction x; the insertion member 20 disposed in the lumen 11 of the shaft 10; the fourth electrode 44 provided on the outer side of the fourth side hole 34; the fourth wire 54 that is electrically connected to the fourth electrode 44 and extends through the fourth side hole 34 to the outer side of the insertion member 20 in the lumen 11 of the shaft 10; and the fixed part 15 in which the shaft 10, the insertion member 20, and the fourth wire 54 are fixed to each other on the proximal side of the fourth side hole 34, the fourth wire 54 having the fourth position 64 and the fifth position 65 inside the shaft 10, the fourth position 64 being located at the same position as the fourth side hole 34 in the longitudinal axis direction x of the shaft 10, the fifth position 65 being located at the same position as the fixed part 15 in the longitudinal axis direction x of the shaft 10, and the fifth position 65 of the fourth wire 54 being located at a position deviated from the fourth position 64 by 90 degrees or more in the circumferential direction of the insertion member 20. According to the catheter 1, since the fourth wire 54 is disposed such that the fifth position 65 is located at the position deviated from the fourth position 64 by 90 degrees or more in the circumferential direction of the insertion member 20, it is possible to provide a margin for a length of the fourth wire 54 in the lumen 11 of the shaft 10. Thus, even if the fourth wire 54 is dragged due to the curving of the shaft 10, such dragging can be absorbed by the extra length, so that the fourth wire 54 can be prevented from propping up. Therefore, the flexibility of a distal end portion of the catheter 1 can be secured.

In the circumferential direction of the insertion member 20, the fifth position 65 of the fourth wire 54 can be located at a position deviated from the fourth position 64 by, for example, 100 degrees or more, 120 degrees or more, 140 degrees or more, or 160 degrees or more. As a result, it is possible to appropriately provide the margin for the length of the fourth wire 54 in the lumen 11 of the shaft 10. In addition, in the circumferential direction of the insertion member 20, the fifth position 65 of the fourth wire 54 may be located at a position deviated from the fourth position 64 by, 270 degree or less, 240 degree or less, 200 degree or less, or 180 degree or less.

In the fixed part 15, the shaft 10, the insertion member 20, and the fourth wire 54 are fixed to each other. As a result, the operating direction of the shaft 10 is regulated, and thus, the shaft 10 can be curved with the fixed part 15 as the base point. In addition, the rotation of the insertion member 20 is suppressed by providing the fixed part 15 in this manner, and thus, it is possible to obtain the shaft 10 which is easily curved two-dimensionally, and to prevent the three-dimensional curving of the shaft 10. Note that the cylinder member 21 of the insertion member 20 is preferably fixed to the shaft 10 and the fourth wire 54 in the fixed part 15.

The fifth position 65, located at the same position as the fixed part 15 in the longitudinal axis direction x of the shaft 10, refers to a range from a distal end to a proximal end of the fixed part 15 in the longitudinal axis direction x.

In order to contribute to the understanding of the present invention, FIG. 3 illustrates a straight line L3 which is parallel to the longitudinal axis direction x and indicates a position deviated from a distal-most position of the longitudinal-axis center of the fourth wire 54 by 90 degrees in the circumferential direction of the insertion member 20 in the fourth position 64.

One or a plurality of the fixed parts 15 can be provided. Although not illustrated, for example, the plurality of fixed parts 15 may be provided side by side in the longitudinal axis direction x of the shaft 10. Note that the fifth position 65 in a case where the plurality of fixed parts 15 are provided side by side in the longitudinal axis direction x of the shaft 10 refers to a range from a distal end of the distal-most fixed part 15 to a proximal end of the proximal-most fixed part 15.

The fixed part 15 is preferably disposed on the proximal side of the proximal-most side hole 30 (the fifth side hole 35 in FIG. 3) provided in the shaft 10.

A length of the fixed part 15 in the longitudinal axis direction x of the shaft 10 is not particularly limited, but is preferably fixed in a range as wide as possible in order to prevent a curving operation from being disabled during use of the catheter 1. Therefore, as illustrated in FIGS. 1 and 3, in the longitudinal axis direction x of the shaft 10, the fixed part 15 is preferably longer than one side hole 30, and more preferably longer than one electrode 40.

As a method for fixing the shaft 10, the insertion member 20, and the fourth wire 54 at the fixed part 15, methods such as brazing such as solder, welding, and adhesion with an adhesive, may be used. FIG. 3 illustrates an example in which the shaft 10, the insertion member 20, and the fourth wire 54 are attached to each other by an adhesive 16 in the fixed part 15.

The fourth side hole 34 is preferably located on the proximal side of a central position of a length from the distal end of the shaft 10 to the distal end of the fixed part 15 in the longitudinal axis direction x of the shaft 10. As a result, even if the fourth wire 54 disposed on the proximal side of the central position of the length from the distal end of the shaft 10 to the distal end of the fixed part 15 is dragged due to the curving of the shaft 10, such dragging can be absorbed by the extra length.

Although not illustrated, the fourth side hole 34 may be the proximal-most side hole 30. As a result, it is possible to prevent the wire 50 connected to the electrode 40 disposed in the proximal-most side hole 30 from propping up.

The fourth wire 54 is preferably wound around the outer side of the insertion member 20 from the fourth position 64 to the fifth position 65. Such winding around the outer side of the insertion member 20 makes it easy to provide the margin for the length of the fourth wire 54 in the lumen 11 of the shaft 10.

The fourth wire 54 may be wound make a round or wound spirally, or a part thereof may have a wave shape, which is similar to the first wire 51.

Hereinafter, matters common to the catheters 1 according to the first to third embodiments will be described.

As illustrated in FIG. 7, it is preferable that the insertion member 20 has: the cylinder member 21 having the distal end and the proximal end in the longitudinal axis direction, the cylinder member 21 having the lumen 11 extending in the longitudinal axis direction; and the elastic member 22 disposed in the lumen 11 of the cylinder member 21, and that the first side hole 31 or the fourth side hole 34 be disposed to face the portion of the short diameter 21A of the ellipse of the cylinder member 21 in a case where the outer shape of the cross section perpendicular to the longitudinal axis direction of the cylinder member 21 is the ellipse having the long diameter 21B and the short diameter 21A. Since the wire 50 is inserted through the side hole 30 toward the lumen 11 of the shaft 10, the space for the wire 50 is required the most near the side hole 30. However, a space in the vicinity of a connection portion between the wire 50 and the electrode 40 can be secured by disposing the side hole 30 to face the portion of the short diameter 21A of the ellipse of the cylinder member 21, and thus, the wire 50 can be easily disposed.

As can be understood from FIG. 1, the shaft 10 is preferably capable of curving in two directions, that is, a normal direction of the first side hole 31 or the fourth side hole 34 and a direction opposite to the normal direction. In detail, in FIG. 1, the distal portion of the shaft 10 can curve in the two directions of the direction A and the direction B opposite to the direction A. Since the position of the side hole 30 and the curve direction of the shaft 10 are set in this manner, it is easy to provide the margin for the length of the first wire 51 or the fourth wire 54 in the lumen 11 of the shaft 10, and the three-dimensional curving of the shaft 10 can also be prevented.

2. Method for Manufacturing Catheter

The present invention also provides a method for manufacturing a catheter. Hereinafter, each step will be described.

First, a shaft is prepared (Step 1), the shaft having a distal end and a proximal end in a longitudinal axis direction, being provided with a first side hole on a wall of the shaft, and having a lumen extending in the longitudinal axis direction. As the shaft, what has been described in "1. Catheter" can be used.

A first wire is inserted into the lumen of the shaft through the first side hole to expose the first wire from the proximal end of the shaft (Step 2). In order to facilitate the insertion of the first wire into the lumen of the shaft, the shaft may be curved at the time of inserting the first wire into the lumen of the shaft through the first side hole.

In Step 2 of exposing the first wire from the proximal end of the shaft, a first electrode is preferably connected to a distal end portion of the first wire. As a result, it is unnecessary to connect the first wire and the first electrode in the subsequent step, and thus, the catheter can be smoothly manufactured.

The insertion member is inserted into the lumen of the shaft (Step 3). As the insertion member, what has been described in "1. Catheter" can be used. Specifically, the insertion member can be inserted from the proximal end of the shaft. It is preferable that at least one of an outer surface of the insertion member and an inner surface of the shaft be coated with a fluororesin in order to enhance slipperiness of the surface of the insertion member and facilitate the insertion into the shaft.

In Step 3 of inserting the insertion member into the lumen of the shaft, the first wire can be disposed in the lumen of the shaft outside the insertion member.

The first wire is pulled in a state where the shaft is curved (Step 4). As a result, it is possible to secure a length of the wire required at the time of curving the shaft. In addition, it is also possible to shape the extending direction of the wire in the lumen of the shaft by pulling the wire. For example, the first wire can be pulled from the proximal side in the pulling step.

In Step 4 of pulling the first wire in the state where the shaft is curved, the curving of the shaft means curving intentionally performed by a worker applying an external force to the shaft from a natural state in which no external force is applied to the shaft or by the own weight of the shaft. Thus, the shaft before being curved in Step 4 includes what is gently curved in a natural state.

In Step 4 of pulling the first wire in the state where the shaft is curved, the shaft may be curved two-dimensionally or may be curved three-dimensionally. A portion of the shaft in the longitudinal axis direction may be curved, and it is preferable to curve a portion where the shaft is to be curved particularly when the catheter is used. For example, in a case where the shaft includes a fixed part fixing the wire and the insertion member, it is preferable to curve a portion of the shaft from the distal end to the fixed part. As a result, the extra length of the first wire can be secured even longer. The shaft may be curved at one point or may be curved at a plurality of points. When the plurality of points of the shaft are curved, it is preferable that curve directions of the respective curved portions be the same.

The shaft can be curved by the worker or the shaft can be curved using a curving jig in a state where the shaft is placed on a horizontal plane such as a work table. In addition, the shaft can be also curved by retaining an intermediate portion of the shaft in the longitudinal axis direction and hanging both end portions in the longitudinal axis direction by its own weight or by applying a predetermined weight.

The proximal portion of the wire may be directly gripped and pulled by the worker, or a pulling member configured to pull the wire may be connected to the proximal portion of the wire and the wire may be pulled by pulling the pulling member.

The curving of the shaft is released (Step 5). Note that Steps 1 to 5 are sequentially performed. As the curving of the shaft is released, the pulling of the first wire is released, sand thus, a part of the first wire is drawn back to the distal side. As a result, it is possible to provide a margin for a length of the first wire in a state where the catheter is not curved. Thus, even if the first wire is dragged by curving the shaft of the catheter during the operation, such dragging can be absorbed by the extra length, so that the prop-up of the first wire can be prevented. Therefore, the flexibility of the distal end portion of the catheter can be secured.

In Step 5 of releasing the curving of the shaft, it is preferable not to apply an external force to the shaft. As a result, the shaft easily returns to the natural state.

In Step 5 of releasing the curving of the shaft, the shaft may be stretched straight. Even such a method can provide the margin for the length of the first wire in the state where the catheter is not curved during the operation. As a method for stretching the shaft straight, a method of placing the shaft inside a mold in which a straight groove is formed, a method in which the worker grips and stretches both the end portions of the shaft in the longitudinal axis direction, or the like can be used. Note that, it is unnecessary to completely return the shaft to the state before the curving in Step 5 of releasing the curving of the shaft, and it is sufficient to release the external force that has been applied to the shaft.

It is preferable that, in Step 1 of preparing the shaft, the shaft be provided with a second side hole on the wall of the shaft on a proximal side of the first side hole, the first side hole and the second side hole being located at positions overlapping with each other in a circumferential direction of the shaft, and that the first side hole and the second side hole be disposed on an outer side a curve in the step of pulling the first wire. Since the position of the side hole at the time of curving is adjusted in this manner, it is easy to provide the margin to the length of the wire in a state where the shaft of the catheter is not curved.

It is preferable that the shaft be provided with a second side hole on the wall of the shaft on a proximal side of the first side hole in Step 1 of preparing the shaft, that a step of inserting a second wire into the lumen of the shaft through a second side hole to expose the second wire from the proximal end of the shaft be further provided before the step of inserting the insertion member into the lumen of the shaft, and that the second wire be also pulled in the step of pulling the first wire. As a result, it is possible to secure the length, required at the time of curving the shaft, for the second wire as well as the first wire. In addition, a working process can also be shortened since it is unnecessary to individually pull the respective wires.

It is preferable to further provide a step of fixing the shaft, the first wire, and the insertion member to each other on the proximal side of the first side hole after Step 5 of releasing the curving of the shaft. As a result, an operating direction of the shaft is regulated, and thus, the shaft can be curved with a fixed part as a base point. In addition, such a fixing enables the shaft which is easily curved two-dimensionally, and it is possible to prevent the three-dimensional curving of the shaft. Note that the description on the fixed part 15 in "1. Catheter" can be referred to regarding an aspect of fixing the shaft, the insertion member, and the first wire.

It is preferable to further provide a step of fixing the shaft, the first wire, and the insertion member to each other on the proximal side of the first side hole before Step 5 of releasing the curving of the shaft and after the step of pulling the first wire. It is also possible to secure the length of the wire required at the time of curving the shaft by fixing the shaft, the first wire, and the insertion member in such a procedure.

This application claims the benefit of the priority date of Japanese patent application No. 2019-185879 filed on Oct. 9, 2019. All of the contents of the Japanese patent application No. 2019-185879 filed on Oct. 9, 2019 are incorporated by reference herein.

REFERENCE SIGNS LIST

1: A catheter
10: A shaft
11: Lumen
12: A wall
15: A fixed part
17: A tip
20: An insertion member
21: A cylinder member
21A: Short diameter
21B: Long diameter
22: An elastic member
25: An operation wire
30: A side hole
31: A first side hole
32: A second side hole
33: A third side hole
34: A fourth side hole
35: A fifth side hole
40: An electrode
41: A first electrode
42: A second electrode
43: A third electrode
44: A fourth electrode
45: A fifth electrode
50: A wire
51: A first wire
52: A second wire
53: A third wire
54: A fourth wire
55: A fifth wire
61: A first position
62: A second position
63: A third position
64: A fourth position
65: A fifth position
70: An operation part
101: A conventional catheter
110: A shaft of a conventional catheter
120: An insertion member of a conventional catheter
130: A side hole of a conventional catheter
140: An electrode of a conventional catheter
150: A wire of a conventional catheter
A, B: A direction
L1: A straight line, which is parallel to the longitudinal axis direction and indicates a position deviated from a distal-most position of the longitudinal-axis center of the first wire by 45 degrees in the circumferential direction of the insertion member in the first position.

L2: A straight line which is parallel to the longitudinal axis direction and indicates a position deviated from the distal-most position by 90 degrees in the circumferential direction of the insertion member.
L3: A straight line which is parallel to the longitudinal axis direction and indicates a position deviated from a distal-most position of the longitudinal-axis center of the fourth wire by 90 degrees in the circumferential direction of the insertion member in the fourth position.
x: A longitudinal axis direction
$\theta 1$: Angle of deviation of second position from first position in circumferential direction
$\theta 2$: Angle of deviation of third position from first position in circumferential direction

The invention claimed is:

1. A catheter comprising:
a shaft having a distal end and a proximal end in a longitudinal axis direction and a lumen extending in the longitudinal axis direction, the shaft having a wall having a first side hole and a second side hole provided adjacently in order from a distal side;
an insertion member disposed in the lumen of the shaft;
a first electrode provided on an outer side of the first side hole; and
a first wire that is electrically connected to the first electrode through the first side hole and extents in the lumen of the shaft but outside the insertion member, wherein
the first wire has a first position and a second position inside the shaft, the first position being located at a same position as the first side hole in the longitudinal axis direction, and the second position being located at a same position as the second side hole in the longitudinal axis direction,
the first wire is wound around the insertion member from the first position to the second position, and
the insertion member comprises:
a cylinder member having a distal end and a proximal end in a longitudinal axis direction, the cylinder member having a lumen extending in the longitudinal axis direction; and
an elastic member disposed in the lumen of the cylinder member, wherein
an outer shape of a cross section perpendicular to the longitudinal axis direction of the cylinder member is an ellipse having a long diameter and a short diameter, and
the insertion member is disposed in the shaft so that the first side hole of the shaft faces a portion of the short diameter of the ellipse of the cylinder member.
2. The catheter according to claim 1, further comprising:
a third side hole is provided on the wall of the shaft on a proximal side of the second side hole, wherein
the first wire has a third position inside the shaft, the third position being located at a same position as the third side hole in the longitudinal axis direction, and
the third position of the first wire is located at a position deviated from the first position by 90 degrees or more in a circumferential direction of the insertion member.
3. The catheter according to claim 1, wherein
the second position of the first wire is located at a position deviated from the first position by 45 degrees or more in a circumferential direction of the insertion member.
4. The catheter according to claim 1, wherein
the first side hole and the second side hole are located at positions overlapping with each other in a circumferential direction of the shaft.

5. The catheter according to claim 1, wherein
the first side hole and the second side hole are located at positions not overlapping with each other in a circumferential direction of the shaft.

6. The catheter according to claim 1, wherein
the shaft, the insertion member, and the first wire are fixed to each other on a proximal side of the second side hole.

7. The catheter according to claim 1, further comprising:
a second electrode provided on an outer side of the second side hole; and a second wire that is electrically connected to the second electrode through the second side hole and extents in the lumen of the shaft but outside the insertion member, wherein
a third side hole is provided on the wall of the shaft on a proximal side of the second side hole,
the second wire has a second position and a third position inside the shaft, the second position being located at a same position as the second side hole in the longitudinal axis direction, and the third position being located at a same position as the third side hole in the longitudinal axis direction, and
the third position of the second wire is located at a position deviated from the second position by 45 degrees or more in the circumferential direction of the insertion member.

8. The catheter according to claim 7, wherein
a direction in which the first wire is wound around the insertion member from the first position to the second position is same as a direction in which the second wire is wound around the insertion member from the second position to the third position.

9. The catheter according to claim 7, wherein
a direction in which the first wire is wound around the insertion member from the first position to the second position is opposite to a direction in which the second wire is wound around the insertion member from the second position to the third position.

10. The catheter according to claim 1, wherein
the shaft is disposed so that the shaft can bend in a direction of a normal direction of the first side hole and a direction opposite to the normal direction.

11. A method for manufacturing the catheter of claim 1, the method comprising:
a step of preparing a shaft having a distal end and a proximal end in a longitudinal axis direction, the shaft having a first side hole on a wall of the shaft and a lumen extending in the longitudinal axis direction;
a step of inserting a first wire into the lumen of the shaft through the first side hole to expose the first wire from the proximal end of the shaft;
a step of inserting an insertion member into the lumen of the shaft;
a step of bending the shaft so as to pull the first wire inwardly toward the lumen of the shaft; and
a step of releasing the the shaft from the bending.

12. The method according to claim 11, wherein
in the step of preparing the shaft, the shaft is provided with a second side hole on the wall of the shaft on a proximal side of the first side hole, the first side hole and the second side hole being located at positions overlapping with each other in a circumferential direction of the shaft, and
the shaft is bent so that the first side hole and the second side hole are disposed on an outer side a curve of the bent shaft in the step of bending the shaft.

13. The method according to claim 11, further comprising
a step of inserting a second wire into the lumen of the shaft through a second side hole to expose the second wire from the proximal end of the shaft before the step of inserting the insertion member into the lumen of the shaft, wherein
the shaft is provided with the second side hole on the wall of the shaft on a proximal side of the first side hole in the step of preparing the shaft, and
the second wire is also pulled in the step of bending the shaft.

14. The method according to claim 11, further comprising
a step of fixing the shaft, the first wire, and the insertion member to each other on the proximal side of the first side hole after the step of releasing the shaft from the bending.

15. The method according to claim 11, further comprising
a step of fixing the shaft, the first wire, and the insertion member to each other on the proximal side of the first side hole before the step of releasing the shaft from the bending and after the step of bending the shaft.

16. A catheter comprising:
a shaft having a distal end and a proximal end in a longitudinal axis direction, the shaft having a fourth side hole provided on a wall of the shaft and a lumen extending in the longitudinal axis direction;
an insertion member disposed in the lumen of the shaft;
a fourth electrode provided on an outer side of the fourth side hole;
a fourth wire that is electrically connected to the fourth electrode through the fourth side hole and extents in the lumen of the shaft but outside the insertion member; and
a fixed part in which the shaft, the insertion member, and the fourth wire are fixed to each other on a proximal side of the fourth side hole, wherein
the fourth wire has a fourth position and a fifth position inside the shaft, the fourth position being located at a same position as the fourth side hole in the longitudinal axis direction, and the fifth position being located at a same position as the fixed part in the longitudinal axis direction,
the fifth position of the fourth wire is located at a position deviated from the fourth position by 90 degrees or more in a circumferential direction of the insertion member, and
the fourth side hole is located on the proximal side of a central position of a length from the distal end of the shaft to a distal end of the fixed part in the longitudinal axis direction.

17. The catheter according to claim 16, wherein
the fourth wire is wound around the insertion member from the fourth position to the fifth position.

18. The catheter according to claim 16, wherein
the insertion member comprises:
a cylinder member having a distal end and a proximal end in a longitudinal axis direction, the cylinder member having a lumen extending in the longitudinal axis direction; and
an elastic member disposed in the lumen of the cylinder member, wherein
an outer shape of a cross section perpendicular to the longitudinal axis direction of the cylinder member is an ellipse having a long diameter and a short diameter, and
the insertion member is disposed in the shaft so that the fourth side hole of the shaft faces a portion of the short diameter of the ellipse of the cylinder member.

19. The catheter according to claim 16, wherein the shaft is disposed so that the shaft can be bent in a direction of a normal direction of the fourth side hole and a direction opposite to the normal direction.

20. A catheter comprising:

a shaft having a distal end and a proximal end in a longitudinal axis direction, the shaft having a fourth side hole provided on a wall of the shaft and a lumen extending in the longitudinal axis direction;

an insertion member disposed in the lumen of the shaft;

a fourth electrode provided on an outer side of the fourth side hole;

a fourth wire that is electrically connected to the fourth electrode through the fourth side hole and extents in the lumen of the shaft but outside the insertion member; and a fixed part in which the shaft, the insertion member, and the fourth wire are fixed to each other on a proximal side of the fourth side hole, wherein the fourth wire has a fourth position and a fifth position inside the shaft, the fourth position being located at a same position as the fourth side hole in the longitudinal axis direction, and the fifth position being located at a same position as the fixed part in the longitudinal axis direction, the fifth position of the fourth wire is located at a position deviated from the fourth position by 90 degrees or more in a circumferential direction of the insertion member; and the insertion member comprises:

a cylinder member having a distal end and a proximal end in a longitudinal axis direction, the cylinder member having a lumen extending in the longitudinal axis direction; and an elastic member disposed in the lumen of the cylinder member, wherein an outer shape of a cross section perpendicular to the longitudinal axis direction of the cylinder member is an ellipse having a long diameter and a short diameter, and the insertion member is disposed in the shaft so that the fourth side hole of the shaft faces a portion of the short diameter of the ellipse of the cylinder member.

21. The catheter according to claim 20, wherein the fourth wire is wound around the insertion member from the fourth position to the fifth position.

22. The catheter according to claim 20, wherein the shaft is disposed so that the shaft can be bent in a direction of a normal direction of the fourth side hole and a direction opposite to the normal direction.

\*     \*     \*     \*     \*